US00PP15157P2

(12) United States Plant Patent
Bradford

(10) Patent No.: US PP15,157 P2
(45) Date of Patent: Sep. 21, 2004

(54) CHERRY TREE NAMED 'GLENOIA'

(50) Latin Name: *Prunus avium*
Varietal Denomination: Glenoia

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 26 days.

(21) Appl. No.: 10/602,668

(22) Filed: Jun. 25, 2003

(51) Int. Cl.[7] ..... A01H 5/00

(52) U.S. Cl. ..... Plt./181

(58) Field of Search ..... Plt./181

(56) References Cited

U.S. PATENT DOCUMENTS

| | | | | |
|---|---|---|---|---|
| PP6,407 P | 11/1988 | Bradford | ..... | Plt./181 |
| PP12,859 P2 | 8/2002 | Bradford | ..... | Plt./181 |

*Primary Examiner*—Anne Marie Grunberg

(57) ABSTRACT

The present invention relates to a cherry tree, *Prunus avium,* and more particularly to a new and distinct variety broadly characterized by a medium size, vigorous, hardy, self-sterile, productive and regular bearing tree. The fruit matures under the ecological conditions described in late May, with first picking on May 25, 2003. The fruit is uniformly large in size, oblate in shape, clingstone in type, firm in texture, red in flesh color, and dark red in skin color. The variety was developed from an open pollinated seed from an undetermined cherry seedling.

1 Drawing Sheet

Botanical classification: *Prunus avium.*

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of cherry tree, which has been denominated varietally as 'Glenoia'. During the spring of 1993 I gathered fruit from several different unnamed cherry seedlings in my experimental orchard at Bradford Farms near La Grand, Calif. in Merced County (San Joaquin Valley). The seeds from this fruit were removed, cracked, stratified, germinated, and grown as seedlings on their own root in my greenhouse, and upon reaching dormancy transplanted to a cultivated area of my experimental orchard described above. During the fruit evaluation season of 1997 I selected several cherry trees that exhibited desirable qualities. The present variety was selected as a single tree from the group described above. Subsequent to origination of the present variety of cherry tree, I asexually reproduced it by budding and grafting in the experimental orchard descried above, and such reproduction of plant and fruit characteristics were true to the original plant in all respects. The reproduction of the variety included the use of 'Colt' (unpatented) rootstock, upon which the present variety was compatible and true to type.

The present variety is most similar to the 'Glenred' (U.S. Plant Pat. No. 12,859) cherry by producing cherries that are large in size, oblate in shape, firm in texture, dark red in skin color, red in flesh color, and sweet in flavor, but is distinguished therefrom and an improvement thereon by blooming about two days later, by producing cherries that ripen about ten days later, and by being a pollinator for both the 'Glenred' cherry and the 'Tulare' (U.S. Plant Pat. No. 6,407) cherry.

SUMMARY OF VARIETY

In summary, the present variety is characterized by a medium size, vigorous, hardy, self-sterile, productive and regular bearing tree. The fruit matures under the ecological conditions described in the latter part of May, with first picking on May 25, 2003. The fruit is uniformly large in size, very sweet in flavor, oblate in shape, clingstone in type, firm in texture, red in flesh color, and full red in skin color.

DRAWING

The accompanying photograph displays a characteristic twig bearing leaves, two fruits with the stems attached, several whole fruits detached from the stems to exhibit the skin color and form, two fruits sectioned along different planes to reveal the flesh and fibers, and two individual leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 26, 2003, on a four year old tree on Colt rootstock. All major color code designations are by reference to the Inter-Society Color Council, National Bureau of Standards. Common color names are also used occasionally.

Tree

Size: Medium, reaching a height of 13' [3.96 m.] and a spread of 9' [2.74 m] after four growing seasons on Colt rootstock.

Vigor: Vigorous, responding typically to irrigation and fertilization. The plant should be grown on a standard commercial rootstock for production purposes.

Growth: Upright.

Form: A natural tendency to generate a central leader system if unpruned, but a vase shape may be obtained by pruning.

Branch angle range: 40 to 80 degrees.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-sterile, must be cross pollinated by another early blooming cherry variety, such as 'Glenred' or 'Tulare'.

Bearing: Regular bearer with no alternate bearing yet observed.

Trunk:

*Size.*—Medium, with a maximum diameter of 2½" [63.5 mm.] after the fourth growing season.

*Texture.*—Somewhat shaggy.

*Bark color.*—Grayish brown [61. gy.Br].

*Lenticels.*—Approximate Number Per Square Inch: 12. Color: Brownish orange [54. brO]. Typical Size: ⅛" to ⅜" [3.2–9.5 mm.].

Branches:

*Main scaffold diameter.*—1¾" [44 mm.] measured 12" above the crotch.

*Limb diameter.*—1⅛" [29 mm.] measured 12" above the first fork.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Grayish brown [61. gy.Br].

*Lenticels.*—Approximate Number Per Square Inch: 15. Color: Brownish orange [54. brO]. Typical size: ⅛" to ¼" [3.2–6.4 mm.].

Leaves:

*Size.*—Medium. Average Length: 5⅛" [130 mm.]. Average Width: 2½" [63.5 mm.].

*Arrangement.*—Alternate.

*Thickness.*—Medium.

*Form.*—Elliptical.

*Apex.*—Acuminate.

*Base.*—Acute, mostly rounded.

*Surface.*—Smooth.

*Color.*—Dorsal Surface: Dark olive green [126. d.OlG]. Ventral Surface: Moderate yellow green [120. m.YG].

*Margin.*—Finely serrate.

*Venation.*—Pinnately net veined.

*Vein color.*—Light yellow green [119. l.YG] to Light reddish brown [42. l.rBr].

*Petiole.*—Average Length: 1 7/16" [35.6 mm.]. Average Thickness: 1/16" [1.6 mm.]. Color: Very dark purplish red [260. v.d.pR] topside and Grayish red [19. gy.R] underside.

*Stipules.*—Number: Typically 2 per leaf. Average Length: 7/16" [11.1 mm.]. Color: Grayish pink [8. gy.Pk] becoming Very deep red [14. v.deep R] when old and dry.

*Glands.*—Number: 2 per leaf. Position: On petiole. Size: Large. Form: Reniform to oval. Color: Very deep red [14. v.deep R] along the edge and Light grayish Red [18. l.gy.R] toward the center.

*Leaf buds.*—Conic.

Flower buds:

*Hardiness.*—Hardy, with respect to central California winters.

*Diameter.*—Typically 5/16" [7.9 mm.] right before bloom.

*Length.*—Typically ⅝" [15.9 mm.] right before bloom.

*Form.*—Free.

*Surface.*—Nonpubescent.

*Color.*—White [263. white].

Flowers: Perfect, complete, perigynous, usually a single pistil, typically twenty or more stamens, five sepals and petal locations alternately positioned.

*Average flower diameter.*—1 5/16" [33.3 mm.].

*Number of petals.*—Usually five.

*Petal shape.*—Circular to oval.

*Petal margin.*—Somewhat wavy with an occasional serration.

*Average petal diameter.*—9/16" [14.3 mm.].

*Average petal length.*—9/16" [14.3 mm.].

*Petal apex.*—Rounded with a small notch located at the top center of the margin on many.

*Petal base.*—Rounded to slightly cuneate.

*Petal color.*—White [263. white].

*Anther color.*—Light yellow [86. l.Y].

*Stigma color.*—Pale yellow green [121. p.YG].

*Sepal color.*—Grayish purplish red [262. gy.pR] over Light yellow green [119. l.YG].

*Sepal length.*—¼" [6 mm.].

*Sepal width.*—5/32" [4 mm. ].

*Average pistil length.*—½" [14.3 mm.].

*Average stamen length.*—9/16" [14.3 mm.].

*Fragrance.*—Moderate.

*Blooming period.*—Early compared with other varieties.

*Onset of bloom.*—Five percent on Mar. 14, 2003, about two days after 'Glenred' and three days before 'Tulare'.

*Date of full bloom.*—Mar. 23, 2003.

*Duration of bloom.*—Five to ten days, dependent on ambient temperature.

*Number per cluster.*—3 to 4 most common.

FRUIT

Maturity when described: Firm ripe, May 26, 2003.

Date of first picking: May 25, 2003.

Date of last picking: May 31, 2003.

Size: Uniform, large.

*Average diameter axially.*—⅞" [22.2 mm.].

*Average cheek diameter.*—1 1/16" [27.0 mm.].

*Average diameter across suture plane.*—15/16" [23.8 mm.].

*Typical weight.*—0.30 ounces [8.6 grams].

Form: Uniform, symmetrical, compressed axially and around the suture.

*Cheek plane form.*—Oblate.

*Suture plane form.*—Oval.

*Axial view form.*—Elliptical.

Suture: An inconspicuous Blackish red [21. blackish R] line located in a shallow trough from the stem cavity but discontinuing at the apex.

Ventral surface: Rounded, slightly lipped toward the apex.

Lips: Equal.

Stem cavity: Flaring, slightly compressed in the suture plane, suture showing on one side.

*Depth.*—3/16" [4.8 mm.].

*Breadth.*—⅜" [9.5 mm.].

Base: Truncate to cordate.

Apex: Rounded, somewhat cordate when viewed along the suture.

Pistil point: An inconspicuous dot depressed within the suture.

Stem: Medium.
*Average length.*—1¾" [44.5 mm.].
*Average width.*—1/16" [1.6 mm.].
*Color.*—Brilliant yellow green [116. brill.YG] with some Grayish red [19. gy.R] tinting from sunlight.
*Attachment.*—Strong.
Skin:
*Thickness.*—Medium.
*Surface.*—Smooth.
*Tenacity.*—Tenacious to flesh.
*Astringency.*—Slightly astringent.
*Tendency to crack.*—Slight after rain, not quite as resistant as 'Tulare'.
*Color.*—Very dark red [17. v.d.R] to Very deep red [14. v.deep R] over the entire surface.
Flesh: Color.—Dark red [16. d.R] with Very deep red [14. v.deep R] streaking near the stone.
*Surface of Pit Cavity.*—Very dark red [17. v.d.R] fibers breaking when twisted from the stone.
*Amygdalin.*—Moderate.
*Juice.*—Abundant, rich.
*Juice color.*—Deep red [13. deep R].
*Texture.*—Very firm, crisp.
*Fibers.*—Abundant, fine.
*Ripens.*—Slightly earlier toward the apex and near the stone.
*Flavor.*—Very sweet with moderate acid, usually 20 to 23 brix.
*Aroma.*—Slight.
*Eating quality.*—Very best.

STONE

Type: Clingstone.
Form: Obovoid.
External color: Light grayish yellowish brown [79. l.gy.yBr].
Pit wall color when cracked: Pale orange yellow [73. p.OY].
Internal cavity color: Light grayish yellowish brown [79. l.gy.yBr].
Average width: ⅜" [9.5 mm.].
Average length: ½" [12.7 mm.].
Average breadth: 5/16" [7.9 mm.].
Hilum: Rounded.
Base: Rounded.
Apex: Acute to rounded.
Sides: Equal.
Surface: Smooth.
Ridges: Two thin ridges along the ventral edge.
Average pit wall thickness: 1/16" [1.6 mm.]
Tendency to split: None observed.
Kernel:
*Form.*—Oval.
*Skin color.*—Yellowish white [92. yWhite] when freshly removed.
*Pellicle color.*—Grayish yellow [90. gy.Y].
*Vein color.*—Pale yellow [89. p.Y].
*Taste.*—Bitter.
*Viable.*—Yes.
*Average width.*—7/32" [5.6 mm.].
*Average length.*—5/16" [7.9 mm.].
*Amygdalin.*—Abundant.

USE

Market: Fresh market and long distance shipping.
Keeping quality: Good. Fruit quality observed to remain in good condition after 14 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and described, that is most similar to the 'Glenred' (U.S. Plant Pat. No. 12,859) cherry by producing cherries that are large in size, oblate in shape, firm in texture, dark red in skin color, red in flesh color, and sweet in flavor, but is distinguished therefrom and an improvement thereon by blooming about two days later, by producing cherries that ripen about ten days later, and by being a pollinator for both the 'Glenred' and 'Tulare' (U.S. Plant Pat. No. 6,407).

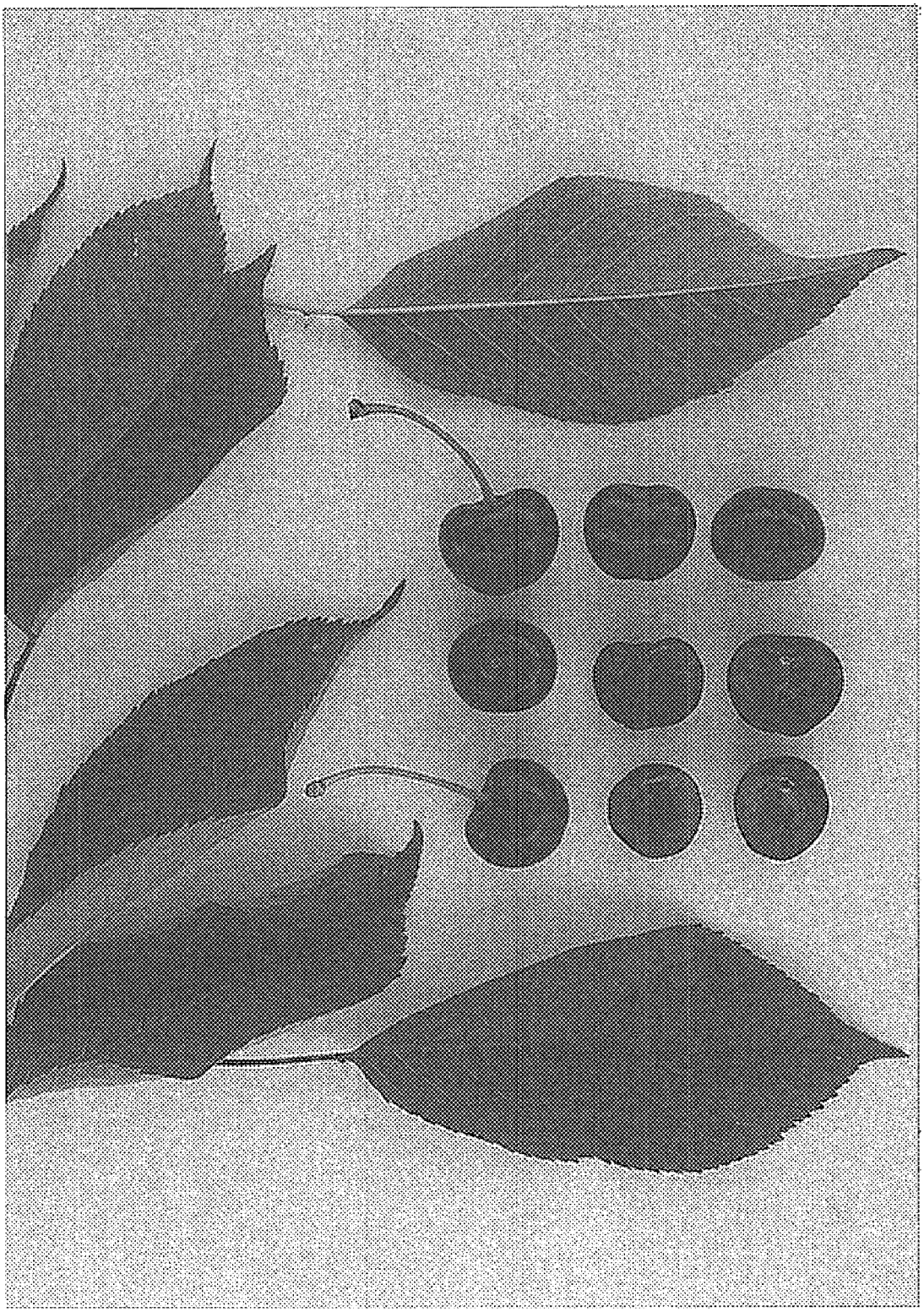

* * * * *